(12) United States Patent
Hall et al.

(10) Patent No.: US 6,316,655 B1
(45) Date of Patent: Nov. 13, 2001

(54) METHOD OF MAKING HYDROXY END-TERMINATED LINEAR SILOXANES

(75) Inventors: Charles Alan Hall, Crestwood, KY (US); Dennis Gene Van Koevering, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/785,685

(22) Filed: Feb. 20, 2001

(51) Int. Cl.$^7$ ........................................... C07F 7/08
(52) U.S. Cl. ................................................ 556/450
(58) Field of Search ................................ 556/450

(56) References Cited

U.S. PATENT DOCUMENTS

| | | | |
|---|---|---|---|
| 3,853,933 | * 12/1974 | Siciliano | 556/450 |
| 3,876,677 | 4/1975 | Wu | 260/448.2 |
| 4,032,557 | 6/1977 | Spork et al. | 260/448.2 |
| 4,217,228 | * 8/1980 | Koerner et al. | 55/450 X |
| 4,395,563 | 7/1983 | Hayes | 556/459 |
| 4,497,942 | 2/1985 | Yeboah et al. | 528/12 |
| 4,609,751 | 9/1986 | Hajjar | 556/456 |
| 5,068,383 | 11/1991 | Bourgoin et al. | 556/452 |
| 5,173,558 | * 12/1992 | Hansen et al. | 556/450 X |
| 5,457,220 | * 10/1995 | Razzano | 556/450 X |
| 5,476,916 | 12/1995 | Pachaly et al. | 528/12 |
| 5,488,125 | 1/1996 | Omura et al. | 556/463 |
| 5,576,408 | 11/1996 | Igarashi et al. | 528/12 |
| 6,184,408 | * 2/2001 | Burns et al. | 556/450 |

* cited by examiner

Primary Examiner—Paul F. Shaver
(74) Attorney, Agent, or Firm—Alan Zombeck

(57) ABSTRACT

A process is disclosed for preparing linear hydroxy end-terminated linear siloxanes comprising the steps of;

a) mixing chlorosiloxanes having the formula

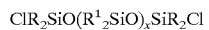

$$ClR_2SiO(R^1{}_2SiO)_xSiR_2Cl$$

where x is an integer having a value from 1–10, each R and $R^1$ is an independently selected monovalent hydrocarbon group, with volatile methyl siloxanes to form a solution of chlorosiloxanes in volatile methyl siloxanes;

b) hydrolyzing the solution of chlorosiloxanes in volatile methyl siloxanes to form a hydrolysis mixture of reaction products;

c) separating the hydrolysis mixture of reaction products into an aqueous phase and a siloxane phase comprising hydroxy end-terminated linear siloxanes and volatile methyl siloxanes; and d) recovering the hydroxy end-terminated linear siloxanes from the siloxane phase.

15 Claims, No Drawings

METHOD OF MAKING HYDROXY END-TERMINATED LINEAR SILOXANES

FIELD OF THE INVENTION

This invention is a process for making hydroxy end-terminated linear siloxanes. In particular, the process involves hydrolyzing a solution of chlorosiloxanes in volatile methyl siloxanes and separating the resulting hydroxy end-terminated linear siloxane products.

BACKGROUND OF THE INVENTION

Hydroxy end-terminated linear siloxanes are an important class of silicone additives useful in many commercial silicone compositions. In particular, short chain hydroxy end-terminated linear siloxanes, that is linear siloxanes having a degree of polymerization of less than 10, perform an essential role in most silicone rubber compositions as a plasticizer because of their high ratio of hydroxy groups to dimethylsiloxy units.

However, short chain hydroxy end-terminated linear siloxanes are not easily manufactured because of their inherent propensity to further polymerize by the additional condensation of the terminal hydroxy groups. Thus, short chain hydroxy end-terminated linear siloxanes are difficult, if not impossible, to make by conventional methods such as via the hydrolysis of dichlorodimethylsilane. Such techniques generally produce linear polydimethylsiloxanes with terminal hydroxy groups having a chain length (degree of polymerization) of 10–12, or a SiOH content of 3–4%. A linear polydimethylsiloxane with a SiOH content of 3–4% often does not function optimally as a plasticizer in silicone rubber compositions, where the effectiveness is proportional to the silanol content. Thus, alternative methods of producing short chain short chain hydroxy end-terminated linear siloxanes, having chain lengths of 2–9 and SiOH contents of 8–10% have been described in the art.

U.S. Pat. No. 5,488,125 to Omura et al. discloses a method for manufacturing organosilanes having silanol groups, useful as dispersing agents in silicone rubber compositions. The method disclosed in the '125 patent involves hydrolyzing an organoalkoxy silane, and in particular dimethyl dimethoxy silane, having at most a 20 ppm content of chlorine, with water having an electroconductivity of at least $10^{10}$ MΩ, then further adding a macro-porous cation exchange resin. Similarly, U.S. Pat. No. 5,576,408 teaches a two-stage hydrolysis of organoalkoxysilanes using a macroporous cation exchange resin and controlling the amount of water in each stage.

U.S. Pat. No. 4,395,563 to Hayes teaches the hydrolysis of alkoxysilanes, and a process for controlling the average chain length of silanol-stopped polysiloxanes. The Hayes patent in particular discloses the preparation of silanol-stopped polydimethylsiloxanes having 2 to 8 siloxane units.

While the prior art methods advantageously control the rate of reaction to provide specific chains of polysiloxanes, these methods also produces substantial quantities of a water/alcoho/siloxane stream that is often treated as a waste-product stream in commercial processes.

The present inventors have discovered a process for preparing hydroxy end-terminated linear siloxanes based on the hydrolysis of chlorosiloxanes. In particular, the present inventors have unexpectedly found a method that avoids or minimizes the further polymerization of the short chain hydroxy end-terminated linear siloxanes, especially with un-reacted chloride terminated polysiloxane reactants.

Furthermore, the present invention does not produce high quantities of waste stream products, as does the method of producing short chain hydroxy end-terminated linear siloxanes based on the hydrolysis of the alkoxysilanes.

The object of the present invention is to provide a process for producing hydroxy end-terminated linear siloxanes.

SUMMARY OF THE INVENTION

The present invention is a process for producing hydroxy end-terminated linear siloxanes comprising the steps of, a) mixing chlorosiloxanes having the formula $$ClR_2SiO(R^1_2SiO)_xSiR_2Cl$$

where x is an integer having a value from 1–10, each R and $R^1$ is an independently selected monovalent hydrocarbon group,
with volatile methyl siloxanes to form a solution of chlorosiloxanes in volatile methyl siloxanes;

b) hydrolyzing the solution of chlorosiloxanes in volatile methyl siloxanes to form a hydrolysis mixture of reaction products;

c) separating the hydrolysis mixture of reaction products into an aqueous phase and a siloxane phase comprising hydroxy end-terminated linear siloxanes and volatile methyl siloxanes; and d) recovering the hydroxy end-terminated linear siloxanes from the siloxane phase.

DETAILED DESCRIPTION OF THE INVENTION

The first step in the process of the present invention is to mix chlorosiloxanes having the formula, $$ClR_2SiO(R^1_2SiO)_xSiR_2Cl \qquad (I)$$

where x has value from 1–10,

R and $R^1$ are alkyl, alkenyl, or aryl groups
with volatile methyl siloxanes to form a solution of chlorosiloxanes in volatile methyl siloxanes.

Chlorosiloxanes that can be used in the first step of the present invention are described by formula (I), as shown above. The chlorosiloxanes may be a single species or a mixture of such siloxanes. The value of x in formula (I) can be from 1 to 10. Preferably x has a value from 1 to 4 and more preferably is 1 or 2. Even more preferred is when the chlorine end-terminated linear siloxane is a mixture of siloxanes of formula (I) where x=1 and x=2. Yet even more preferred is when the ratio of siloxanes where x=1 to siloxanes where x=2 is 1.5:1.

R and $R^1$ is an independently selected monovalent hydrocarbon group. The R and $R^1$ substituents in formula (I) can independently be an alkyl, alkenyl, or aryl group. Examples of alkyl groups as R and $R^1$ substituents can include methyl, ethyl, propyl, isopropyl, or butyl. Examples of alkenyl groups as R and $R^1$ substituents can include vinyl or allyl groups. Preferably R and $R^1$ is an alkyl group, and most preferably R and $R^1$ is methyl.

The chlorosiloxanes are well known in the art and can be prepared by any of the methods known in the art. In particular, the chlorosiloxanes can be prepared by the catalyzed redistribution of polyorganosiloxanes as taught in U.S. Pat. No. 5,068,383, which is hereby incorporated by reference. Using the processes taught in the '383 patent, chloride end-terminated polyorganosiloxanes are redistributed over an alumina, silica-alumina, activated carbon, zeolites, or acid clay catalyst to produce the chloride end-terminated linear siloxane having the desired chain length.

The volatile methyl siloxanes used in the present invention can be cyclic methyl siloxanes, linear methyl siloxanes, or mixtures thereof. Representative linear volatile methyl siloxanes are hexamethyldisiloxane with a boiling point of 100° C., viscosity of 0.65 mm$^2$/s, and formula Me$_3$SiOSiMe$_3$; octamethyltrisiloxane with a boiling point of 152° C., viscosity of 1.04 mm$^2$/s, and formula Me$_3$SiOMe$_2$SiOSiMe$_3$; decamethyltetrasiloxane with a boiling point of 194° C., viscosity of 1.53 mm$^2$/s, and formula Me$_3$SiO(Me$_2$SiO)$_2$SiMe$_3$; dodecamethylpentasiloxane with a boiling point of 229° C., viscosity of 2.06 mm$^2$/s, and formula Me$_3$SiO(Me$_2$SiO)$_3$SiMe$_3$; tetradecamethylhexasiloxane with a boiling point of 245° C., viscosity of 2.63 mm$^2$/s, and formula Me$_3$SiO(Me$_2$SiO)$_4$SiMe$_3$; and hexadecamethylheptasiloxane with a boiling point of 270° C., viscosity of 3.24 mm$^2$/s, and formula Me$_3$SiO(Me$_2$SiO)$_5$SiMe$_3$. The volatile methyl siloxanes can also be a mixture of linear methyl siloxanes described above.

The cyclic methyl siloxanes have the general formula [(CH$_3$)$_2$SiO]$_z$. The value of z can be 3–8, but is preferably 4–6. The cyclic methyl siloxanes useful in the present invention have a boiling point less than 250° C. and a viscosity of 0.65–5.0 centistokes (mm$^2$/s). Some representative cyclic methyl siloxanes are hexamethylcyclotrisiloxane [(Me$_2$)SiO]$_3$; octamethylcyclotetrasiloxane [(Me$_2$)SiO]$_4$; decamethylcyclopentasiloxane [(Me$_2$)SiO]$_5$; and dodecamethylcyclohexasiloxane [(Me$_2$)SiO]$_6$. The volatile methyl siloxanes can also be a mixture of the cyclic methyl siloxanes described above. Furthermore, the volatile methyl siloxane can be a mixture of cyclic and linear methyl siloxanes.

Preferably the volatile methyl siloxane is a cyclic methyl siloxane. Most preferably, the volatile methyl siloxane is octamethylcyclotetrasiloxane.

The chlorosiloxanes can be mixed with the volatile methyl siloxanes by any conventional mixing techniques to form a solution, i.e. a homogeneous mixture of chlorosiloxanes in volatile methyl siloxanes.

The chlorosiloxanes to volatile methyl siloxanes can be mixed at weight ratios varying from 1/0.33 to 1/10. A weight ratio ranging from 1/1 to 1/5 is preferred, and a ratio ranging from 1/2 to 1/4 is the most preferred.

Step (b) of the present invention process involves hydrolyzing the solution of chlorosiloxanes in volatile methyl siloxanes to form a hydrolysis mixture of reaction products. This step is performed by contacting the solution of chlorosiloxanes in volatile methyl siloxanes with either water or an aqueous HCl solution. When an aqueous HCl solution is used, the concentration of HCl can vary from 0.01 to 18% HCl by weight. Preferably, the concentration of the aqueous HCl solution is from 1 to 10% wt % HCl, and most preferably is 2 to 8 wt % HCl.

The hydrolysis reaction of step (b) can be conducted at a temperature between 0° C. and 90° C., and at various pressures. Preferably, the hydrolysis reaction is conducted at ambient conditions, usually about 25° C. and at atmospheric pressure.

Step (c) in the present process involves separating the hydrolysis mixture of reaction products into an aqueous phase and a siloxane phase containing a mixture of hydroxy end-terminated linear siloxanes and volatile methyl siloxanes. Preferably, the separation is accomplished via phase separation techniques. Phase separation involves allowing the reaction mixture of products to stand, that is, without mixing, until the siloxane phase containing the volatile methyl siloxanes and hydroxy end-terminated linear siloxanes separates from the aqueous phase into two distinct layers. The bottom aqueous layer is then removed, preferably by draining the bottom aqueous layer from the phase separation vessel.

Optionally, the siloxane phase resulting from step c) can be further subjected to a chloride reduction step by means known in the art, for example, by contacting the resulting siloxane phase from step c) with water, a basic aqueous solution, a buffered aqueous solution, ion exchange resins, or molecular sieves, to lower the chloride content of the siloxane phase. If this additional step is performed, the resulting aqueous phase is again phase separated from the siloxane phase according to step c.

Step (d) in the process of the present invention involves recovering the hydroxy end-terminated linear siloxanes from the siloxane phase. The recovering step can be accomplished by any number of techniques known in the art, such as vacuum stripping the volatile methyl siloxanes and distilling the hydroxy end-terminated linear siloxane. Preferably the hydroxy end-terminated linear siloxane is fractionally distilled under controlled conditions to avoid any further condensation of the siloxane to higher molecular polymers.

In a preferred embodiment of the present invention, the total amount of HCl in the process is controlled by monitoring the concentration of HCl in the resulting aqueous phase following step b) of the process. For purposes of this invention, the weight % concentration of HCl in the resulting aqueous phase following step b) of the process is referred to as the outlet % HCl. Thus, the outlet % HCl in the process is affected by the selection of the chlorosiloxane, the ratio of mixing the chlorosiloxane in volatile methyl siloxanes, the ratio of the aqueous phase to the solution of chlorosiloxanes in volatile methyl siloxanes, and if used in step b), the concentration of the aqueous HCl solution. Preferably, the outlet % HCl is from 3 to 13 wt % HCl, and most preferably is from 7 to 9 wt % HCl.

The process of the present invention can be performed in a batch, semi-batch, or continuous mode.

The following examples are provided to illustrate the present invention and are not intended to limit the claims thereof.

EXAMPLES

Reactions were conducted in a 1000 mL baffled glass unit. The reaction medium was agitated at a mixing speed of 2000 rpm with a four bladed flat turbine having a diameter of 2.5 in (6.35 cm) and a blade height of 0.0875 in (0.222 cm), providing a tip speed of 22 ft/sec (6.7 m/s).

The chlorosiloxanes, hereafter abbreviated as CEBx, where x designates the degree of polymerization in formula (I),

Cl—R$_2$SiO(R$^1$$_2$SiO)$_x$SiR$_2$—Cl  (I)

were prepared according to the methods of U.S. Pat. No. 5,068,383 and batch distilled to yield pure fractions. The various CEBx materials were then mixed with octamethyltetrasiloxane in varying ratios.

The chlorosiloxanes and octamethyltetrasiloxane were premixed, in the desired proportions, and gravity fed to the reaction unit containing the desired quantity of the aqueous phase. The mixture was stirred for 90 seconds to ensure complete hydrolysis had occurred.

Following hydrolysis, the reaction mixture was drained through a hydrophobic membrane to separate the siloxane and aqueous phases.

The siloxane phase was then added back to the mixing vessel and water added at a 1:2 water/siloxane ratio and mixed for 90 seconds to wash the siloxane, thereby reducing the amount of chloride in the siloxane phase.

The hydroxy end-terminated linear siloxanes were separated from the volatile methyl siloxanes via vacuum distillation. The volatile methyl siloxanes were distilled from the mixture to leave behind the hydroxy end-terminated linear siloxanes. In a typical run, a 1"(2.54 cm) inner diameter column with 10 sieve trays on a 1"(2.54 cm) spacing was mounted on a 500 mL round bottom flask, fitted with thermometer, feed funnel, water-cooled condenser, and collection funnel. Approximately 400 mL of the siloxane phase was loaded in the round bottom flask, and another 600 mL in a feed funnel. As distillate was collected in the overhead funnel, additional siloxane phase was fed to the round bottom flask so as to keep a constant volume. The runs were complete when the overhead temperature indicated all octamethyltetrasiloxane was removed from the siloxane phase mixture (100° C. at 15 mm Hg, or 2 kPa of pressure). Then, the heat and vacuum were turned off, and the product collected from the round bottom flask.

The number average molecular weight ($M_n$) of the hydroxy end-terminated siloxanes were analyzed using gas chromatography by first reacting the silanol groups with bis(trimethyl-silyl)trifluoroacetamide (BSTFA). Trifluoroacetic acid was added to catalyze the reaction. Approximately 1 mL of BSTFA and 1 drop of trifluoroacetic acid were added to approximately 0.5 mL of the sample in a vial. After standing for 20 minutes at room temperature, the sample was injected into the gas chromatograph. The gas chromatograph used was a Hewlett-Packard 5890.

Example 1

Using the above general procedures, 27 runs were conducted to demonstrate the effects of the following; the dilution ratio of chlorine end-terminated linear siloxane to volatile methyl siloxanes, calculated as the volume fraction of chlorine end-terminated siloxanes to volatile methyl siloxanes and designated vol fraction CEB; the ratio of chlorine end-terminated linear siloxane having a degree of polymerization of 1 and 2 (that is x=1 or 2 according to formula 1 described above), calculated as the mole fraction of chlorine end-terminated siloxane with a degree of polymerization of 2 to a degree of polymerization of 1 and designated as mole fraction CEB2/CEB1; the ratio of the aqueous phase to the siloxane phase, calculated as the volume fraction of water and designated vol fraction $H_2O$; the weight percent HCl in the aqueous phase; and the outlet weight % HCl which is the final weight percent HCl in the resulting aqueous phase after the hydrolysis reaction.

The hydrolysis process of the present invention was evaluated by measuring three important parameters of the resulting siloxane phase; the percentage of the hydroxy end-terminated linear siloxane having a degree of polymerization of 2–4, designated as % L2–L4; the number average molecular weight (Mn), which provides a direct correlation to the overall % silanol content of the polymer and the percentage linears siloxanes in the hydrolysis product, that is the mixture of linear siloxanes and volatile methyl siloxanes, designated as wt % linears. The wt % linear siloxane indicates how much cyclic siloxanes are produced in the hydrolysis reaction.

The results of the 27 runs are summarized in Table I.

TABLE I

| Run | Mole frac CEB2/CEB1 | Vol frac CEBx | Vol frac $H_2O$ | % HCl | Outlet % HCl | Wt % linears | Mn | % L2–L4 |
|---|---|---|---|---|---|---|---|---|
| 1 | .25 | .25 | .67 | 3.5 | 6.4 | 13.7 | 353.4 | 58.0 |
| 2 | .25 | .25 | .80 | 3.5 | 8.6 | 11.6 | 372.9 | 51.3 |
| 3 | .25 | .25 | .80 | 0 | 1.5 | 13.3 | 346.1 | 59.9 |
| 4 | .25 | .25 | .43 | 7.2 | 14.6 | 10.8 | 470.9 | 22.6 |
| 5 | .25 | .25 | .43 | 7.2 | 7.6 | 13.8 | 363.6 | 51.8 |
| 6 | .42 | .20 | .67 | 3.5 | 5.6 | 11.7 | 339.9 | 70.0 |
| 7 | .42 | .33 | .67 | 3.5 | 7.0 | 18.3 | 368.7 | 56.1 |
| 8 | .08 | .20 | .67 | 3.5 | 6.9 | 10.0 | 346.8 | 56.0 |
| 9 | .08 | .33 | .67 | 3.5 | 7.5 | 17.3 | 398.3 | 38.2 |
| 10 | .42 | .25 | .67 | 7.2 | 9.8 | 12.6 | 381.2 | 51.9 |
| 11 | .08 | .25 | .67 | 7.2 | 10.2 | 12.0 | 404.3 | 36.6 |
| 12 | .42 | .25 | .67 | 0 | 2.7 | 15.45 | 335.7 | 70.0 |
| 13 | .08 | .25 | .67 | 0 | 3.1 | 13.6 | 344.5 | 52.3 |
| 14 | .25 | .25 | .67 | 3.5 | 6.4 | 13.6 | 352.2 | 58.6 |
| 15 | .25 | .20 | .80 | 3.5 | 4.7 | 9.6 | 342.2 | 65.8 |
| 16 | .25 | .20 | .43 | 3.5 | 9.5 | 10.5 | 368.6 | 51.3 |
| 17 | .25 | .33 | .80 | 3.5 | 5.4 | 16.6 | 371.9 | 51.4 |
| 18 | .25 | .33 | .43 | 3.5 | 13.3 | 13.8 | 504.7 | 16.9 |
| 19 | .25 | .20 | .67 | 7.2 | 9.4 | 9.8 | 367.6 | 53.9 |
| 20 | .25 | .20 | .67 | 0 | 2.3 | 11.1 | 327.5 | 67.0 |
| 21 | .25 | .33 | .67 | 7.2 | 10.9 | 15.0 | 430.2 | 32.5 |
| 22 | .25 | .33 | .67 | 0 | 3.9 | 19.3 | 357.7 | 53.8 |
| 23 | .42 | .25 | .80 | 3.5 | 4.8 | 13.6 | 347.5 | 67.4 |
| 24 | .42 | .25 | .43 | 3.5 | 10.4 | 12.6 | 396.0 | 45.8 |
| 25 | .08 | .25 | .80 | 3.5 | 5.0 | 12.2 | 361.3 | 51.3 |
| 26 | .08 | .25 | .43 | 3.5 | 11.4 | 12.0 | 430.9 | 27.9 |
| 27 | .25 | .25 | .67 | 3.5 | 6.4 | 14.1 | 354.1 | 57.8 |

Example 2

Additional runs were conducted to further demonstrate the effects of selected process variables. The reaction conditions and procedures were the same as described above. The results are summarized in Table II.

TABLE II

| Run | Mole frac CEB2 | Vol frac CEBx | Vol frac $H_2O$ | % HCl | Outlet % HCl | Wt % linears | Mn | % L2–L4 |
|---|---|---|---|---|---|---|---|---|
| 28 | .44 | .25 | .60 | 1.3 | 5.0 | 15.1 | 343.2 | 66.3 |
| 29 | .44 | .25 | .60 | 3.2 | 6.9 | 14.5 | 353.3 | 62.7 |
| 30 | .44 | .33 | .60 | 0 | 4.9 | 19.7 | 357.8 | 59.5 |
| 31 | .44 | .33 | .60 | 1.9 | 6.8 | 18.8 | 370.7 | 55.0 |
| 32 | .44 | .33 | .80 | 5.1 | 6.9 | 17.2 | 371.8 | 55.9 |
| 33 | .76 | .25 | .60 | 1.6 | 5.0 | 16.6 | 344.3 | 75.2 |
| 34 | .76 | .25 | .60 | 3.4 | 6.7 | 15.5 | 352.01 | 71.0 |
| 35 | .60 | .25 | .60 | 1.5 | 5.0 | 15.9 | 343.2 | 71.2 |
| 36 | .60 | .25 | .60 | 3.2 | 6.8 | 14.9 | 353.4 | 66.4 |

What is claimed is:
1. A process for producing hydroxy end-terminated linear siloxanes comprising:
 a) mixing chlorosiloxanes having the formula

 $ClR_2SiO(R^1{}_2SiO)_xSiR_2Cl$ where x is an integer having a value from 1–10, each R and $R^1$ is an independently selected monovalent hydrocarbon group,
with volatile methyl siloxanes to form a solution of chlorosiloxanes in volatile methyl siloxanes;
 b) hydrolyzing the solution of chlorosiloxanes in volatile methyl siloxanes to form a hydrolysis mixture of reaction products;

c) separating the hydrolysis mixture of reaction products into an aqueous phase and a siloxane phase comprising hydroxy end-terminated linear siloxanes and volatile methyl siloxanes; and d) recovering the hydroxy end-terminated linear siloxanes from the siloxane phase.

2. The process of claim 1 where the solution of chlorosiloxanes in volatile methyl siloxanes is hydrolyzed with a 0.01–18% by weight aqueous HCl solution.

3. The process of claim 2 where the solution of chlorosiloxanes in volatile methyl siloxanes is hydrolyzed with a 1.0–10.0% by weight aqueous HCl solution.

4. The process of claim 1 where the chlorosil oxanes is mixed with volatile methyl siloxanes at a weight ratio of 1:0.33 to 1:10 to form a solution.

5. The process of claim 4 where the chlorosiloxanes is mixed with volatile methyl siloxanes at weight ratio of 1:2 to 1:4 to form a solution.

6. The process of claim 1 where x has a value from 1 to 4.

7. The process of claim 6 where x has a value from 1 to 2.

8. The process of claim 7 where the ratio of chlorosiloxanes having an x value of 1 to chlorosiloxanes having an x value of 2 is 2:1 to 1:2.

9. The process of claim 8 where the ratio of chlorosiloxanes having an x value of 1 to chlorosiloxanes having an x value of 2 is 1.5:1.

10. The process of claim 1 where the volatile methyl siloxane is octamethyltetrasiloxane, decamethylpentasiloxane, dodecamethylcyclohexane, or mixture thereof.

11. The process of claim 10 where the volatile methyl siloxane dimethyl cyclic siloxane is octamethyltetrasiloxane.

12. The process of claim 1 wherein the hydroxy end-terminated linear siloxanes are recovered from the siloxane phase by a distillation process.

13. The process of claim 1 further comprising a chloride reduction step following the phase separation step c), whereby the siloxane phase containing hydroxy end-terminated linear siloxanes is contacted with water, a basic aqueous solution, a buffered aqueous solution, ion exchange resins, or molecular sieves to produce a siloxane phase having a reduced chloride content.

14. The process of claim 1 whereby the aqueous phase has a concentration of HCl of 3 to 13% by weight.

15. The process of claim 14 whereby the aqueous phase has a concentration of HCl of 7 to 9% by weight.

* * * * *